United States Patent [19]

Olson

[11] 4,337,769
[45] Jul. 6, 1982

[54] PRESSURE INFUSION MODULE

[75] Inventor: Raymond G. Olson, Niles, Ill.

[73] Assignee: Baxter Travenol Laboratories, Inc., Deerfield, Ill.

[21] Appl. No.: 174,489

[22] Filed: Aug. 1, 1980

[51] Int. Cl.³ .............................................. A61M 5/00
[52] U.S. Cl. ........................ 128/214 F; 128/DIG. 12; 222/386.5
[58] Field of Search ........... 128/214 R, 214 E, 214 F, 128/214.2, DIG. 12; 222/95, 97, 103, 386.5

[56] References Cited

U.S. PATENT DOCUMENTS

| | | | |
|---|---|---|---|
| 2,389,134 | 11/1945 | Brown | 138/45 |
| 2,454,929 | 11/1948 | Kenpton | 138/45 |
| 2,500,750 | 3/1950 | Halenza | 137/69 |
| 2,593,315 | 4/1951 | Kraft | 138/45 |
| 2,775,984 | 1/1957 | Dahl | 138/45 |
| 2,781,058 | 2/1957 | Warhns | 138/45 |
| 3,121,445 | 2/1964 | Wisnewski | 138/45 |
| 3,445,043 | 5/1969 | Bull | 222/386.5 |
| 3,556,040 | 1/1971 | Vrbick | 137/517 |
| 3,595,232 | 7/1971 | Leibinsohn | 128/214 |
| 3,734,351 | 5/1973 | Gavdin | 128/214 X |
| 3,780,732 | 12/1973 | Leibinsohn | 128/214 F |
| 4,181,140 | 1/1980 | Baynam et al. | 137/68 R |
| 4,187,847 | 2/1980 | Loeser | 128/214 F |

FOREIGN PATENT DOCUMENTS 1013635 7/1977 Canada .......................... 128/214 X Primary Examiner—Stephen C. Pellegrino
Attorney, Agent, or Firm—Paul C. Flattery; John P. Kirby, Jr.; Garrettson Ellis

[57] ABSTRACT

A liquid administration device comprises a flexible, collapsible bag for the liquid, an outlet tube communicating with the bag and a rigid housing enclosing the bag with the outlet tube projecting outwardly therefrom. Flexible, compressed cellular material is positioned within the housing, exerting pressure due to its compression on the bag which tends to urge the bag towards its collapsed position. Thus the liquid in the bag can be expelled through the outlet tube, with the flow governed by a valve, in a manner independent of gravity.

20 Claims, 4 Drawing Figures

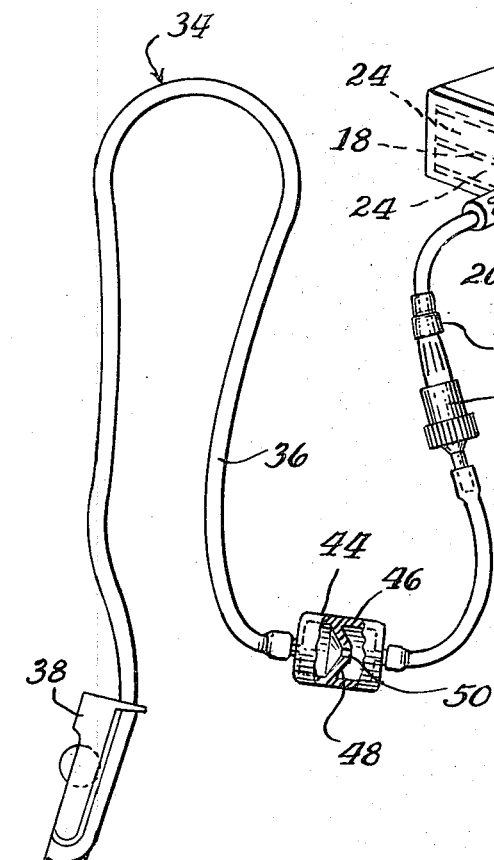
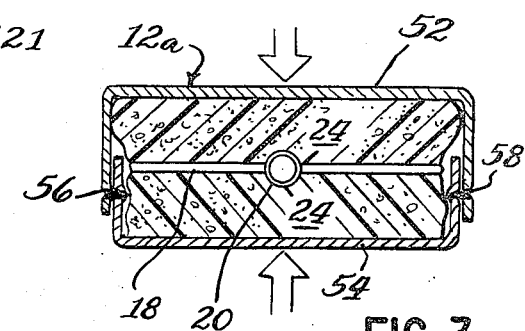
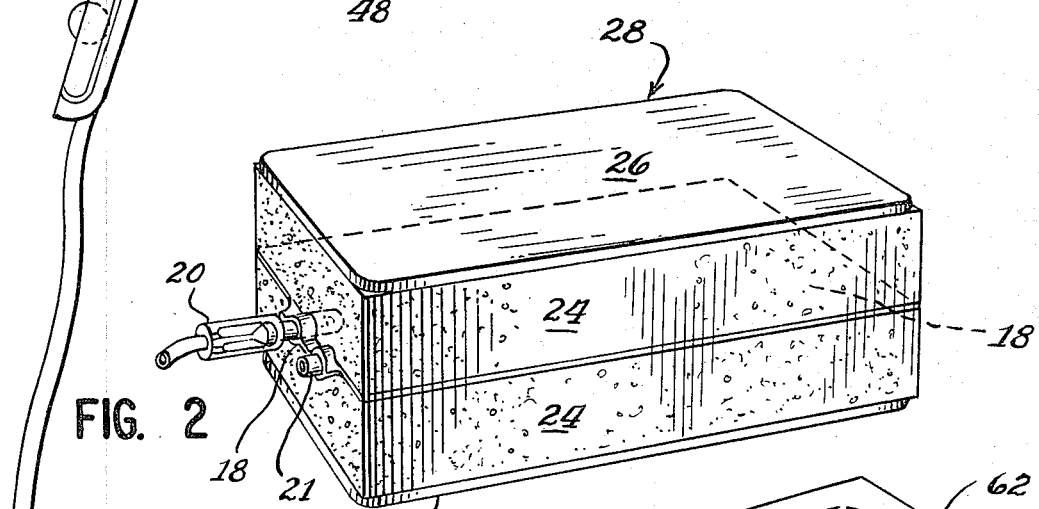
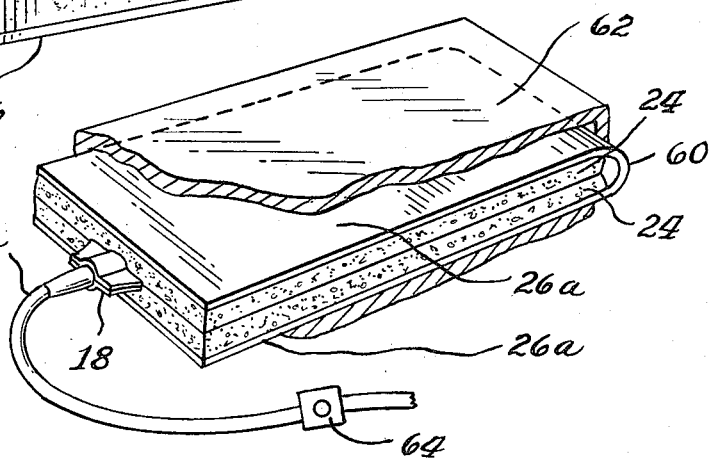

PRESSURE INFUSION MODULE

BACKGROUND OF THE INVENTION

In U.S. Pat. Nos. 3,595,232; 3,734,351; 3,780,732; and 4,187,847, among others, apparatus for the pressure infusion of blood and parenteral solutions is disclosed. Pressurized infusion of parenteral solutions and blood is desirable in some circumstances, since the infusion can be performed independent of gravity, for example when the infusion must be performed at an accelerated rate under emergency conditions.

Also, the Fenwal Division of Baxter Travenol Laboratories, Inc. sells a pneumatically inflatable pressure cuff for surrounding a blood bag and pressurizing it so that blood may be administered from a blood bag within the pressure cuff at a greatly accelerated rate by pneumatic pressurization of the cuff, for example in the instance of a patient with a severe hemorrhage.

However, in the prior art, pressure infusion devices have been expensive and cumbersome, utilizing springs and pressure plates, or requiring pneumatic pumps and the like. There is a need for inexpensive, compact pressure infusion devices which can be stored in the scarce space of an ambulance or a field hospital, since one major desirable use of gravity-free pressure infusion systems is in areas away from the hospital such as on the battle field. Similarly, at the site of an accident, where blood and parenteral solutions must be administered under non-clinical conditions, for example in a moving ambulance, it may be inconvenient to elevate the liquid material for administration to take advantage of conventional gravity flow administration.

Furthermore, there is a need for a convenient, simple, inexpensive, and preferably wearable system for administering small amounts of critical medications over a period of hours while the patient is ambulatory. For example, a diabetic patient may desirably be administered insulin on a generally continuous basis over a 24-hour period, with a total of about 5 mil., for example, being administered. Such a continuous administration of insulin more closely simulates the physiology of the normal functioning of the pancreas in the healthy individual.

Similarly, it is generally agreed that it would be desirable in numerous circumstances to administer a small amount of medicament on a continuous basis over a 24-hour period if it can be conveniently done while the patient is ambulatory. Specifically, continuously administered heparin and other medicament are disclosed in the article by Blackshear in the December, 1979 issue of *Scientific American*, pages 66 to 71.

In accordance with this invention, an optionally wearable module for pressure administration of liquids is provided for the administration of small amounts of medicament over a period of hours, or for the administration of any fluid material in medical or other fields, including liquids or gases as may be desired. The simple pressure administration module may be of about the size of a deck of cards and adapted to administer only a few cubic centimeters of medicament over a period of hours. Alternatively, if desired, an administration module in accordance with this invention may be utilized which contains a liter or more of solution, for accurate administration of parenteral solutions in a manner independent of gravity.

DESCRIPTION OF THE INVENTION

In accordance with this invention, a liquid administration device is provided which comprises a flexible, collapsible bag for the liquid, which is preferably intended for parenteral administration, but may also be used in any other desired manner.

An outlet tube communicates with the bag, and a rigid housing encloses the bag with the outlet tube projecting outwardly therefrom.

In accordance with this invention, flexible, compressed cellular material is positioned within the housing and exerting pressure on the bag tending to urge the bag towards its collapsed position, to expel the liquid through the outlet tube when any such liquid is present in the bag.

Valve means are generally provided to control liquid outflow through the outlet tube. The valve means may comprise a simple roller clamp or other conventional parenteral solution tubing clamp in the circumstance where substantial amounts of parenteral solution are being administered through the device of this invention. However, in the circumstance where only a very few cubic centimeters of medicament or the like are being administered over a period of hours, the valve means is preferably a needle valve or the like, capable of providing a very small adjustable flow orifice to control the slow flow rate of the medicament over the period of hours, as may be desired.

The outlet tube may be joined to a length of flexible tubing having an I.V. needle at its other end, with the flexible tubing carrying the adjustable flow valve means described above to control flow through the outlet tube.

Also, sealing valve means may be provided to control liquid outflow from the outlet tube on an on-off basis. For example, a frangible closure of the type shown in U.S. Pat. No. 4,181,140 may be used, or any other desired on-off valve which preferably is of the type which resides in the flexible tube, and may be opened by manual manipulation from the exterior of the flexible tube.

The bag and compressed cellular material may be positioned between a pair of relatively stiff plate members in the housing. The plate members facilitate the assembly of the device in that they permit compression of the entire structure so that it may be inserted with ease into the housing.

Specifically, the plate members may be joined together at one end to form a U-shaped structure, for simplicity and ease of assembly.

The liquid-containing bag utilized herein may be placed on one side of a single pad of flexible, compressed cellular material, or it may be sandwiched between a pair or more of pads of the flexible cellular material.

If desired, the rigid housing may define a hollow tube having a bore of rectangular cross section to receive the sandwiched array of the bag for liquids and the compressed cellular material. The rigid housing may define closed ends to form a factory-sealed module, with the outlet tube projecting out of an aperture in one end.

Alternatively, the rigid housing may comprise a pair of housing halves brought together about the flexible, compressed cellular material and the bag for the infusion liquid, to compress the structure, with means for retaining the housing halves together in a position compressing the cellular material. Also, a combination of both cellular material and gas-filled bladder means may be used if desired.

It also may be desirable for the outlet tube to communicate with means for reducing the dependence of flow rate on pressure. Such means are generally known, and examples of such are disclosed in U.S. Pat. Nos. 2,389,134; 2,454,929; 2,500,750; 2,775,984; 2,781,058; 2,593,315; 3,121,445; and 3,586,040.

However, preferably it is contemplated for the dependence-reducing means to comprise a chamber, and a conical rubber member pointing upstream and sealed at its periphery therein, and defining an aperture at the apex. Accordingly, increased pressure tends to collapse the conical member to reduce the diameter of the aperture, while decreased pressure permits the conical member to expand to increase the diameter of the aperture. The sensitivity of a valve for reducing the system's dependence on pressure can be varied by adjustment of the durometer of the conical rubber member. A soft rubber member will be more sensitive to relatively low pressure changes so that pressure changes of the fluid within the housing, resulting from changing conditions of expansion of the cellular material during drainage of the bag will be reflected to a lesser extent downstream, because of the presence of the flow rate dependence-reducing means of this invention.

In preparing the device of this invention for providing parenteral solution or the like to a patient independent of the force of gravity and without the need for an auxiliary pump, the flexible, collapsible bag may be positioned against the cellular material so that the cellular material is compressed and the entire structure is inserted into a rigid housing, so that it is continuously subjected to collapsing pressure while the collapsible bag is in its collapsed position.

Preferably, thereafter the parenteral or other liquid is inserted into the collapsible bag, to expand the bag and further compress the cellular material, followed by the step of temporarily sealing the bag to prevent the immediate discharge of the liquid therefrom. This technique provides an effective method for assembly of the device, and permits the bag to be properly inserted into the housing in a spread-out condition, without wrinkles, as may be desirable.

As previously stated, the use of the relatively stiff plate members to sandwich the bag and the compressible cellular material facilitates the insertion of such a structure into the housing by squeezing the plate members to reduce the thickness of the composite structure and inserting the composite structure into the bore of the rigid housing so that the bag, compressed cellular material, and plate members reside in the housing in compressed form, with the bag being pressed into its collapsed position. As stated above, the parenteral liquid is then preferably inserted into the bag by insertion or pumping to expand the bag and further compress the cellular material, followed by temporary sealing of the outlet tube or tubes until the parenteral liquid is desired for administration.

Referring to the drawings,

FIG. 1 is a perspective view of one embodiment of the liquid administration device of this invention.

FIG. 2 is a perspective, fragmentary view of the interior structure of the rigid housing as disclosed in FIG. 1, when removed from the rigid housing.

FIG. 3 is a transverse sectional view of a modified form of the rigid housing structure.

FIG. 4 is a fragmentary perspective view, with portions broken away, of another embodiment of the structure of the rigid housing.

Referring to FIG. 1, a liquid administration device 10 as shown is specifically adapted for parenteral liquid administration.

Rigid housing 12 may be made of molded plastic, and is shown to define a hollow tube having a bore of rectangular cross section. Ends 14, 16 may be closed if desired with a plastic wall which may be integrally molded to housing 12, or added on after the molding process by solvent sealing or the like. Typically, wall 16 is added after housing 12 has been loaded.

As shown in FIG. 2, the contents of housing 12 may include, flexible, collapsible bag 18, sealed at its periphery, and with an outlet tube 20 projecting outwardly therefrom, and an auxiliary filling port 21, which typically remains inside of wall 16 of housing 12. Port 21 may be closed with a needle-pierceable, resealing latex plug so that bag 18 may be filled with a hypodermic syringe or the like.

It may be desired, as shown in FIG. 1, to provide a breakaway connector 22 within outlet tubing of a design, for example, as shown in U.S. Pat. No. 4,181,140. Likewise, other valve structures may be utilized here as a substitute for breakaway closure 22 as may be desired.

Bag 18 may be filled with a parenteral solution. In the case of a small, wearable system, the parenteral solution may comprise about 5 cc. of a medicament such as insulin, heparin, a cancer chemotherapy agent, an antibiotic, a hormone, or any other material in which a critical continuous dosage is desirably administered to the patient.

Alternatively, the bag 18 and its housing 12 may be large, and may contain a liter or more of parenteral solution, in the circumstance where it is desired to provide a gravity-independent administration device for conventional parenteral solution.

Bag 18 is shown to be sandwiched between a pair of pads of compressed flexible, cellular material 24, for example polyurethane foam, flexible styrofoam, cellulose acetate sponge, foam rubber material, or any other desired porous or spongy, flexible material of cellular structure, for example open-cell or closed-cell foam materials.

The pair of cellular pads 24 and bag 18 are then sandwiched between a pair of plates 26, which may be made of metal, fiberboard, relatively stiff plastic, or the like, to provide a sandwiched structure 28 as shown in FIG. 2.

To load sandwiched structure 28 into housing 12, it may be compressed by squeezing of plates 26 and allowed to slide into the bore of housing 12, prior to installation of end piece 16.

As stated above, this procedure is preferably accomplished with bag 18 in a flat, empty condition. Following this insertion step, the contents of bag 18 may be pumped or injected into the bag through tubing 21. Following this, end piece 16 may be attached with tubing 20 projecting through an aperture in the end piece 16.

Connector member 30, attached to tubing 20, is provided for further connection with a conventional luer-type connector 32 of an administration set 34. Administration set 34 may comprise lengths of flexible tubing 36 which may carry a conventional flow control device 38. The specific flow control device in FIG. 1 is shown to be a roller clamp, but it is contemplated that any desired flow control device may be used, and in the event of small quantity, long-term administration it is generally desirable for an accurate needle valve or the like to be used for precise flow control.

Set 34 also may carry a flow measuring means, if desired. Needle 42 is provided at its free end for connection with the venous system of the patient.

Set 34 may optionally be initially separate from liquid administration device 10, and may be connected at the time of use, so that a desired set 34 may be linked with housing 12 and its contents.

Valve means 44 may also be provided in set 34 for reducing the dependence of the flow rate through the set on pressure, to compensate for variable pressure that may be encountered within housing 12 as liquid is drained from bag 18 and the cellular pads 24 are allowed to expand to some extent.

Valve means 44 comprises a chamber 46, within which is positioned a conical rubber member 48, sealed at its periphery and defining an aperture 50 at its apex. Conical member 48 points upstream as shown. Accordingly, increased pressure upstream of the conical member 48, relative to the downstream pressure, tends to collapse the conical member to reduce the diameter of aperture 50. Increased pressure across the conical member permits it to expand to increase the diameter of the aperture. The effect of this is to tend to equalize flow through set 34, irrespective of variation of pressures within housing 12.

Another flow restricter site in the system may be found at needle 42, which will preferably be of a very narrow gauge in those circumstances where the flow rate is expected to be very slow. Hence needle 42 contributes to the flow restriction of the system which, in turn, governs the rate of drainage of liquid from bag 18.

Referring to FIG. 3, a modification of the rigid housing of FIG. 1 is disclosed with the structure of the embodiment being identical to that of FIG. 1, except as otherwise described and shown. Rigid housing 12a constitutes in this case a pair of housing halves 52, 54 which interlock together by means of high frequency welds 56, 58 or the like between housing halves 54. Cellular pads 24, bag 18, and tube 20 may be of similar design to the previous embodiment. For assembly of this structure, pads 24 may sandwich bag 18, and the resulting structure may be placed in housing half 54. Housing half 52 is then brought down onto housing half 54 as shown, and squeezed together as welds 56, 58 are formed, causing the housing 12a to retain cellular pads 24 in compressed relation. The structure may then be used in a manner similar to that described above.

Referring to FIG. 4, another modification of the invention is shown in which bag 18 is sandwiched between the pair of cellular pads 24, in which plate members 26a may be made of fiberboard, cardboard, or the like, and are joined together at one end 60 to form a U-shaped structure enclosing cellular pads 24 and bag 18. This structure, in turn, is inserted into housing 62, which may be of identical design to housing 12.

Tubing 20a may be integrally connected to a flow control member, for example needle valve 64 for precise low volume metering of the pressurized liquid within bag 18. The remainder of tubing 20 may proceed on to a needle 42 and other structures carried by set 34 as may be desired.

If desired, only a single cellular pad 24 may be used on one side of bag 18, with the other pad 24 being omitted in devices of this invention. Likewise, multiple cellular pads may be used on either or both sides of bag 26 in any configuration capable of collapsing bag 18 when tube 20 is open.

The above has been offered for illustrative purposes only, and is not intended to limit the invention of this application, which is as defined in the claims below.

That which is claimed is:

1. A liquid administration device which comprises a flexible, flat collapsible container for liquid, an outlet tube communicating with said container and a rigid housing enclosing said container with said outlet tube projecting outwardly therefrom, the improvement comprising, in combination:

flexible, compressed cellular material positioned within said housing and exerting pressure on said container tending to urge said container toward its flat collapsed position and to expel said liquid through said outlet tube when any such liquid is present in the container.

2. The infusion device of claim 1 in which valve means are provided to control liquid outflow through said outlet tube, and said container is a bag.

3. The infusion device of claim 2 in which said bag is enclosed between a pair of relatively stiff assembly plate members positioned within said housing, said compressed, cellular material also being positioned between said plate members.

4. The infusion device of claim 3 in which said plate members are joined together at one end to form a U-shaped structure.

5. The infusion device of claim 2 in which said bag is sandwiched between a pair of pads of said flexible, compressed, cellular material.

6. The infusion device of claim 1 in which said outlet tube is joined to a length of flexible tubing having an I.V. needle at its other end, said flexible tubing carrying adjustable flow valve means to control flow through said outlet tube and length of flexible tubing, and second, sealing valve means in addition to said flow valve means for added flow control through said flexible tubing.

7. The infusion device of claim 6 in which said length of flexible tubing carries flow measuring means.

8. The infusion device of claim 2 in which said rigid housing defines a hollow tube having a bore of rectangular cross section.

9. The infusion device of claim 8 in which said rigid housing defines closed ends, with said outlet tube projecting out of an aperture in one end.

10. A parenteral liquid infusion device which comprises a flexible, flat collapsible bag for parenteral liquid, an outlet tube communicating with said bag, and a rigid housing defining a hollow tube having a bore of rectangular cross section, said rigid housing enclosing said bag in said bore with said outlet tube projecting outwardly therefrom; flexible, compressed cellular material positioned within said bore on both sides of said bag and exerting pressure on said bag tending to urge it toward its flat collapsed position and to expel said parenteral liquid through said outlet tube when any such parenteral liquid is present in the bag; and valve means to control liquid outflow through the outlet tube.

11. The infusion device of claim 10 in which said bag and flexible, compressed cellular material is enclosed between a pair of relatively stiff assembly plate members positioned in the bore of said housing.

12. The infusion device of claim 11 in which said outlet tube is joined to a length of flexible tubing having an I.V. needle in its other end, said flexible tubing carrying adjustable flow valve means to control flow through said outlet tube and length of flexible tubing when said first valve means is opened.

13. The infusion device of claim 12 in which said length of flexible tubing carries flow rate measuring means.

14. The method of preparing a parenteral liquid infusion device capable of spontaneously providing parenteral solution to a patient independent of the force of gravity and without the need of auxiliary pumps, which comprises:
   inserting into a rigid housing a flexible, collapsible bag for parenteral liquid, positioned against sufficient flexible cellular material so that the cellular material is compressed within said housing and exerting collapsing pressure on said bag, said collapsible bag being in its collapsed position; and
   thereafter inserting parenteral liquid into said collapsible bag to expand the bag and further compress said cellular material, and temporarily sealing said bag to prevent the immediate discharge of parenteral liquid therefrom.

15. The method of claim 14 which comprises joining an outlet of said bag to a length of flexible tubing having an I.V. needle at its other end, and thereafter deactivating the sealing of said bag, whereby the parenteral liquid is spontaneously discharged through said flexible tubing.

16. The method of preparing a parenteral liquid infusion device capable of administering parenteral liquid in a manner independent of gravity and without auxiliary pumps, which comprises:
   laying flexible, compressible cellular material against a flexible, collapsible bag having an outlet tube for parenteral liquid;
   enclosing said bag and compressible cellular material between a pair of relatively stiff plate members;
   squeezing said plate members to reduce the thickness of the composite structure and inserting the composite structure into the bore of a rigid housing, whereby said bag, compressed cellular material, and plate members reside in the housing with the cellular material in compressed form and the bag being pressed into its collapsed position;
   thereafter inserting parenteral liquid through said outlet tube into the bag to expand the bag and further compress said cellular material; and
   temporarily sealing said outlet tube until the parenteral liquid is desired for administration.

17. The method of claim 16 in which separate pads of flexible, compressed cellular material are positioned on opposite sides of said bag.

18. The method of claim 17 in which said outlet tube is thereafter joined to a length of flexible tubing having an I.V. needle at its other end, and controlling flow through said outlet tube and length of flexible tubing by means of adjustable flow valve means after the first valve means has been opened.

19. A parenteral liquid infusion device comprising a flexible, flat collapsible bag for parenteral liquid, an outlet tube communicating with said bag, valve means to control liquid outflow through said outlet tube, a rigid housing enclosing said bag with said outlet tube projecting outwardly therefrom, flexible compressed cellular material positioned within said housing and exerting pressure on said bag tending to urge said bag toward its flat collapsed position and to expel liquid through said outlet tube when any such liquid is present in said bag, said rigid housing comprising a pair of housing halves brought together about said flexible compressed cellular material and bag and to compress said cellular material, and means for retaining said housing halves together in a position compressing said cellular material.

20. A parenteral liquid infusion device comprising a flexible, flat collapsible bag for parenteral liquid, an outlet tube communicating with said bag; valve means to control liquid outflow through said outlet tube; a rigid housing enclosing said bag with said outlet tube projecting outwardly therefrom; flexible compressed cellular material positioned within said housing and exerting pressure on said bag tending to urge said bag toward its flat collapsed position and to expel liquid through said outlet tube when any such liquid is present in said bag, said outlet tube further communicating with means for reducing the dependence of flow rate on pressure, said means comprising a chamber, and a conical rubber member pointing upstream and sealed at its periphery therein, and defining an aperture at the apex, whereby increased pressure tends to collapse said conical member to reduce the diameter of said aperture and decreased pressure permits said conical member to expand to increase the diameter of said aperture.

* * * * *